US009675580B2

(12) United States Patent
Kim et al.

(10) Patent No.: US 9,675,580 B2
(45) Date of Patent: Jun. 13, 2017

(54) METHOD OF TREATMENT FOR ENHANCING EXERCISE PERFORMANCE

(71) Applicant: Kyong-Tai Kim, Pohang-si, Gyeongsangbuk-Do (KR)

(72) Inventors: Kyong-Tai Kim, Pohang-si (KR); Bo-Hwa Choi, Pohang-si (KR); Hoe-Yune Jung, Gyeongju-si (KR); Jae-Cheon Shin, Gyeongju-si (KR); Sang-Taek Oh, Pohang-si (KR); Myung-Su Kang, Pohang-si (KR)

(73) Assignee: Kyong-Tai Kim, Pohang-si, Gyeongsan (KR)

( * ) Notice: Subject to any disclaimer, the term of this patent is extended or adjusted under 35 U.S.C. 154(b) by 0 days.

(21) Appl. No.: 15/058,065

(22) Filed: Mar. 1, 2016

(65) Prior Publication Data

US 2016/0175277 A1 Jun. 23, 2016

Related U.S. Application Data

(62) Division of application No. 14/435,424, filed as application No. PCT/KR2013/008372 on Sep. 16, 2013, now abandoned.

(30) Foreign Application Priority Data

Oct. 11, 2012 (KR) ........................ 10-2012-0113176

(51) Int. Cl.
*A61K 31/352* (2006.01)
*A61K 9/00* (2006.01)
*A23L 33/105* (2016.01)

(52) U.S. Cl.
CPC .......... *A61K 31/352* (2013.01); *A23L 33/105* (2016.08); *A61K 9/0053* (2013.01); *A23V 2002/00* (2013.01)

(58) Field of Classification Search
CPC .................................................. A61K 31/352
USPC ....................................................... 549/400
See application file for complete search history.

(56) References Cited

U.S. PATENT DOCUMENTS

2012/0252887 A1 10/2012 Ahrens et al.

FOREIGN PATENT DOCUMENTS

| JP | 2000-319154 A | 11/2000 |
|---|---|---|
| JP | 2011-105763 A | 6/2011 |
| JP | 2013-542924 A | 11/2013 |
| KR | 10-0407399 B1 | 11/2003 |
| KR | 10-0526164 A | 11/2005 |
| KR | 10-0599496 B1 | 7/2006 |
| KR | 10-0692099 B1 | 3/2007 |
| KR | 10-0701272 B1 | 3/2007 |
| KR | 10-2008-0035378 A | 4/2008 |
| KR | 10-1120996 B1 | 3/2012 |
| KR | 10-1121737 B1 | 3/2012 |
| WO | 02/15901 A1 | 2/2002 |
| WO | 2012/037023 A1 | 3/2012 |

OTHER PUBLICATIONS

XP-002754672, Database WPI, Week 201317, Thomson Scientific, London, GB; AN 2013-C46191 & TW 201 234 973 A (Scent Blaster Corp), Sep. 1, 2012.
European Search Report dated Mar. 7, 2016 of corresponding European Patent Application No. 13844872.5-6 pages.
De Boer et al., "SIRT1 stimulation by polyphenols is affected by their stability and metabolism", Mechanisms of Ageing and Development, 2006, vol. 127, pp. 618-627.
Ehrenborg et al., "Regulation of Skeletal Muscle Physiology and Metabolism by Peroxisome Proliferator-Activated Receptor . delta.", Pharmacological Reviews, 2009. vol. 61, No. 3, pp. 373-393.
Jung et al., "Myricetin suppresses UVB-induced wrinkle formation and MMP-9 expression by inhibiting Raf", Biochemical Pharmacology, 2010, vol. 79, pp. 1455-1461.
International Search Report and its English translation dated Feb. 3, 2014 of PCT/KR2013/008372 which is the parent application—6 pages.
Pratte et al., Behavioural Brain Research, 2011, vol. 216, pp. 313-320.
Medina, et al., FEBS Lett., 1985, vol. 180, No. 1, pp. 77-80.
Handschin et al., Endocrine Reviews, 2006, vol. 27, pp. 728-735.
Nakar et al., Cell, 2008, vol. 134, pp. 405-415.
Auwerx et al., Cell, 2006, vol. 127, pp. 1109-1122.

*Primary Examiner* — Taofiq A Solola
(74) *Attorney, Agent, or Firm* — Knobbe Martens Olson & Bear LLP

(57) ABSTRACT

Provided is a composition containing myricetin or a pharmaceutically available salt thereof as an active ingredient. The composition increases exercise capacity and enhances physical strength. In addition, the composition prevents aging and recovers from fatigue. The composition increases energy efficiency by improving the function of mitochondria, and also has an antiobesity effect by increasing energy consumption. Therefore, the composition may be significantly applied in a functional food or medicine field.

5 Claims, 5 Drawing Sheets

METHOD OF TREATMENT FOR ENHANCING EXERCISE PERFORMANCE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

1. Field of the Application

The present invention relates to a composition containing myricetin or a pharmaceutically available salt thereof as an active ingredient to enhance exercise capacity or recover from fatigue.

2. Discussion of Related Art

While paying so much attention to beauty and health, contemporary people are suffering from obesity, high blood pressure and other types of adult diseases, and although much effort has been exerted in trying to prevent aging, aging is not prevented due to air pollution and excessive stress. To prevent such various types of adult diseases and aging, regular exercise is most effective and economical, but time for exercise is limited, and therefore, various types of medicine for increasing an exercise effect are commercially provided. In addition, athletics combine scientific training, diet and ergogenic aids according to types of sports to set a new record. Among these, the ergogenic aids are frequently used by ordinary people because of the effects for enhancing exercise capacity and removing fatigue factors generating fatigue which are accumulated in the body during physical activity.

Studies relating to functional adjuvants for enhancing exercise capacity are actively performed in the East or West. Now, commercially available products generally include steroid, caffeine, sodium hydrogen carbonate and sodium citrate. However, an effect of such an ingredient is merely a temporary phenomenon, and due to resistance to the ingredient, a product including a higher amount of the ingredient is provided, and a fatal side effect on health may be caused. Accordingly, recently, studies for developing functional adjuvants using natural substances assuring safety such as plant extracts have been actively progressing.

In the conventional art relating to recovery from fatigue or enhancement of exercise capacity using a natural substance, there are a composition for a functional black garlic and tomato drink containing a Korean mistletoe extract (Korean Patent No. 10-1121737), a composition for enhancing exercise capacity and fatigue recovery, which has ginsenosides Rg3 and Rg2 (Korean Patent No. 10-1120996), and a composition for enhancing exercise capacity capability (Korean Patent No. 10-0526164), but their effects or uses are limited.

A flavonol derivative, myricetin, is a main ingredient of the bark of Chinese Bayberry, which is used as an Eastern medicine, and used as a drug for stomatitis, diuretic, a depressant, etc. It is known that myricetin is also included in clover seeds, leaves of Lysimachia christinae, Korean rhododendron, and succedanea, other than Chinese Bayberry. It has been reported that myricetin has various effects on treating cancer, preventing and treating Alzheimer's disease, preventing inflammation, and preventing and treating diabetes. In the Republic of Korea, patents relating to various uses of myricetin are registered. For example, a pharmaceutical composition for preventing or treating liver cancer (Korean Patent No. 1005994960000), a skin cosmetic composition for inhibiting activity of 3β-hydroxysteroid dehydrogenase (Korean Patent No. 1006920990000), and a composition for inhibiting white hair and stimulating growth of black hair (Korean Patent No. 1007012720000) are disclosed. However, a function of enhancing exercise capacity or recovering from fatigue has not been reported yet.

In the study on an ergogenic aid and a physical strength enhancer derived from a natural substance, which has no side effect and is safe, the inventors first found the excellent effects of myricetin on enhancing exercise capacity and physical strength, and therefore completed the present invention.

SUMMARY OF THE APPLICATION

The present invention is directed to providing a composition containing myricetin or a pharmaceutically available salt thereof as an active ingredient to enhance exercise capacity or recover from fatigue. The present invention is also directed to providing a composition containing myricetin or a pharmaceutically available salt thereof as an active ingredient to prevent aging and obesity.

However, technical objects accomplished by the present invention are not limited to the above-described objects, and thus other objects should be clearly understood from the following descriptions by those of ordinary skill in the art.

One aspect of the present invention provides pharmaceutical and food compositions containing myricetin or a pharmaceutically available salt thereof as an active ingredient to enhance exercise capacity or recover from fatigue.

Another aspect of the present invention provides pharmaceutical and food compositions containing myricetin or a pharmaceutically available salt thereof as an active ingredient to prevent obesity.

The composition may be administered into an individual. The "individual" used herein means a target having a disease to be treated, and includes, particularly, humans, or non-human mammals such as primates, mice, rats, dogs, cats, horses and cattle.

The pharmaceutical composition of the present invention may include at least one pharmaceutically available carrier, in addition to the above-described active ingredient, and may be prepared in various dosage forms for administration.

The pharmaceutical composition of the present invention may be applied through oral or parenteral administration (e.g., intravenous, subcutaneous, abdominal or local administration) according to a desired method, and a dosage may vary depending on a patient's body weight, age, sex, health condition, diet, duration, administration method, excretion rate, or severity of a disease.

An exemplary dosage of the pharmaceutical composition of the present invention may vary depending on a condition and body weight of a patient, severity of a disease, a drug type, an administration route or duration, but may be suitably selected by those of ordinary skill in the art. However, the pharmaceutical composition of the present invention is preferably administered at 0.001 to 100 mg/kg of body weight, and more preferably, at 0.01 to 30 mg/kg of body weight per day. The administration may be performed once or several times a day.

The food composition of the present invention may be added to health functional food to enhance exercise capacity or recover from fatigue. When the myricetin or a pharmaceutically available salt thereof is used as a food additive, it may be added alone or in combination with other food or a food additive such as glucose, fructose, sucrose, maltose, sorbitol, stevioside, rubsoside, corn syrup, lactose, citric acid, tartaric acid, maltic acid, succinic acid, lactic acid, L-ascorbic acid, d1-α-tocopherol, sodium erythorbate, glycerin, propyleneglycol, glycerin fatty ester, poly gylcerin fatty ester, sucrose fatty ester, sorbitan fatty ester, gum arabic, carrageenan, casein, gelatin, pectine, agar, a vitamin B group, nicotinamide, calcium pantothenate, an amino acid, a calcium salt, a pigment, a flavor or a preservative, and may be appropriately used according to a conventional method. A mixing amount of the active ingredient may be suitably determined according to a purpose of use (prevention, health or therapeutic treatment). Generally, in the manufacture of food or beverage, the myricetin or pharmaceutically available salt thereof of the present invention may be added at 15 wt % or less, and preferably, 10 wt % or less with respect to the source material. However, for health and hygiene or long-term intake to control health, the amount may be lower than the above range, and since there is no problem in safety, the active ingredient may be used more than the above range.

There is no limit to a type of the food. The food may include a dairy product, soup, a beverage, tea, a drink, an alcoholic beverage, and a vitamin complex, and also include health functional food in its usual acceptation.

In one exemplary embodiment of the present invention, the composition increases exercise endurance, strengthens strength, enhances a sense of balance, and increases exercise adaptation.

In another exemplary embodiment of the present invention, the myricetin increases the oxidative metabolism in mitochondria by increasing the expression of a PGC-1α, NRF-1 or PPAR-δ gene.

Still another aspect of the present invention provides pharmaceutical and food compositions containing myricetin or a pharmaceutically available salt thereof as an active ingredient to recover from fatigue or prevent aging. Here, the recovery of fatigue or the prevention of aging may be enhanced by increasing the expression of an SIRT-1 gene.

The myricetin of the present invention may be extracted from a source material such as a bark of Chinese Bayberry, clover seeds, leaves of lysimachia christinae, Korean rhododendron, succedanea or walnut, and purified myricetin may be purchased in the market. However, a source of the myricetin is not limited thereto.

A composition containing myricetin or a pharmaceutically available salt thereof as an active ingredient enhances exercise capacity and strengthens physical strength. In addition, the composition enhances the prevention of aging and recovery from fatigue. The composition of the present invention improves the function of mitochondria to increase energy efficiency and energy consumption, and also has an antiobesity effect.

BRIEF DESCRIPTION OF THE DRAWINGS

FIG. 4A is a graph showing the expression level of a PGC-1α gene in the mouse myotube due to myricetin, FIG. 4B is a graph showing an expression level of an NRF-1 gene in the mouse myotube due to myricetin, FIG. 4C is a graph showing an expression level of a PPAR-δ gene in the mouse myotube due to myricetin, and FIG. 4D is a graph showing an expression level of a SIRT-1 gene in the mouse myotube due to myricetin.

FIG. 5A is a graph showing an effect of myricetin on reduction of a body weight, and FIG. 5B is a graph showing an effect of myricetin on a change in food intake.

DETAILED DESCRIPTION OF EXEMPLARY EMBODIMENTS

Figure 1:
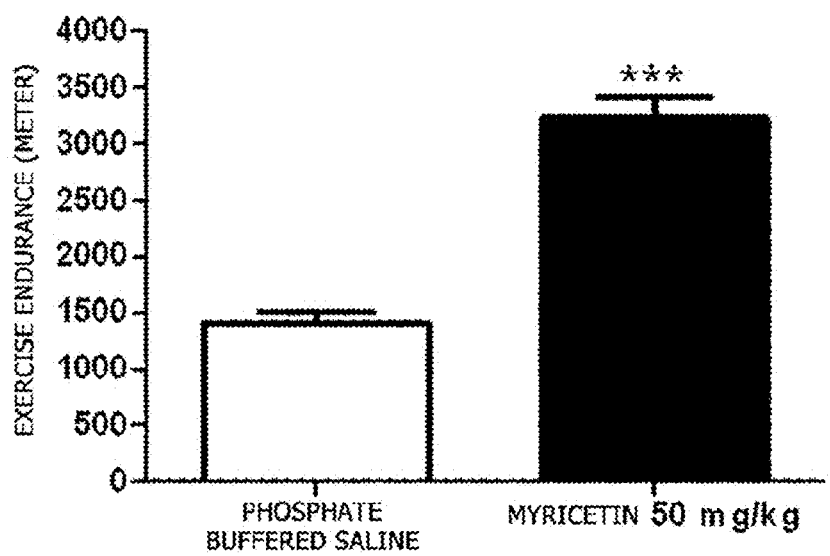
FIG. 1 is a graph showing the enhancement in endurable exercise capacity due to myricetin intake.

Exemplary embodiments of the present application will be described in detail below with reference to the accompanying drawings. While the present application is shown and described in connection with exemplary embodiments thereof, it will be apparent to those skilled in the art that various modifications can be made without departing from the spirit and scope of the application.

The IUAPC name of a compound of the present invention, myricetin, is 3,5,7-trihydroxy-2-(3,4,5-trihydroxyphenyl)-4-chromenone, and a structure of the compound is as follows.

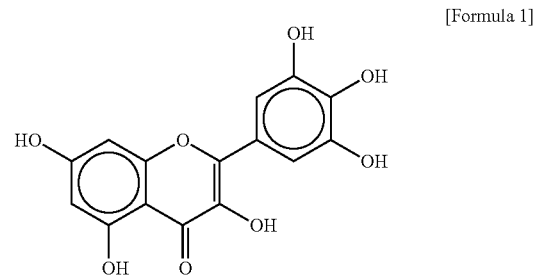

[Formula 1]

The myricetin may be isolated from Chinese Bayberry, clover seeds, leaves of lysimachia christinae, Korean rhododendron, or succedanea, but herein, was purchased from Sigma-Aldrich Co.

In Examples 1 to 4, effects of the myricetin were observed after the myricetin was administered into mice. In Example 1, effects of the myricetin on strengthening physical strength and enhancing endurance were examined, and in Example 2, the maximum power of a muscle was measured. In Example 3, a sensorimotor function was measured, and in Example 4, the expression of genes involved in the biosynthesis and function of mitochondria, exercise capacity and an antiaging activity were measured. In Example 5, an antiobesity effect of the myricetin was measured. Throughout Examples 1 to 5, the effects and use of the myricetin were determined.

Hereinafter, to help in understanding the present invention, exemplary examples will be provided. However, the following examples are merely provided to more easily understand the present invention, not to limit the scope of the present invention.

EXAMPLES

Example 1

Measurement of Effect of Myricetin on Strengthening Physical Strength of Mouse 1-1. Preparation of Myricetin-Administered Group and Negative Control Ten 8-week-old ICR mice were purchased from KOATECH, precultured for 1 week, and then divided into two groups, each group having five mice.

The first group was set up as a negative control by administering phosphate buffered saline, and to the second group, myricetin was orally administered daily at a concentration of 50 mg/kg for two weeks.

1-2. Measurement of Effect of Myricetin on Enhancing Endurance Exercise Capacity and Physical Strength To measure a change in endurance exercise capacity due to myricetin, the animals in the negative control and the myricetin-administered group were run on a treadmill (Panlab&Harvard, Spain).

An exercise performance protocol was configured to make the mice run until exhaustion at 25 cm/sec for 20 minutes, 30 cm/sec for 20 minutes, 33 cm/sec for 20 minutes, 36 cm/sec for 20 minutes and 36 cm/sec for 15 minutes with a gradient of 5°, and 30 cm/sec for 15 minutes and 41 cm/sec with a gradient of 10°.

To adapt the mice to running on the treadmill, the day before the experiment, they were run at 27 cm/sec for 10 minutes with a gradient of 5°.

The mice were not fed for two hours before the running on the treadmill on the day of the experiment, and then the maximum exercise capacity of the experimental animals was measured after the running on the treadmill. The time to determine the maximum exercise capacity was defined as the time at which the experimental animals were behind 20 seconds or more the speed of the treadmill, or a cumulative number of electric shocks approached 100 times within 5 minutes. A significance of the experiment result was verified by performing a t-test for the test group and the control group, and the results showed a statistically significant difference (***$p<0.0005$).

As the result, as shown in FIG. 1, it was noted that the myricetin-administered mice can be run on the tread mill longer. Accordingly, it was determined that the myricetin intake contributes greatly to strengthening physical strength. Therefore, it was noted that myricetin can be used as an adjuvant for enhancing the physical strength.

Example 2

Measurement of Effect of Myricetin on Enhancing Grip Strength of Mouse 2-1. Preparation of Myricetin-Administered Group and Negative Control To measure an effect of myricetin on enhancing endurance exercise capacity of a mouse, ten 8-week-old ICR-series mice having a body weight of 30±5 g were used. As described in Example 1, the experimental animals were divided into two groups. The first group was determined as a negative control, and to the second group, myricetin was orally administered daily at a concentration of 50 mg/kg for two weeks.

2-2. Measurement of Effect of Myricetin on Strengthening Grip Strength of Mouse

To measure a change in the maximum strength of a muscle due to myricetin, a grip strength test (Bioseb, France) was performed on the animals in the control group and the myricetin-administered group.

Maximum grip strengths of the front paws and rear paws were measured by pulling a tail of the mouse backward while the mouse grabbed a grip strength tester. The grip strength was measured three times, and an average value was used. A significance of the experimental result was verified by performing a t-test on each of the test group and the control group, and the result showed a statistically significant difference ($p<0.005$, **$p<0.00005$).

Figure 2A:
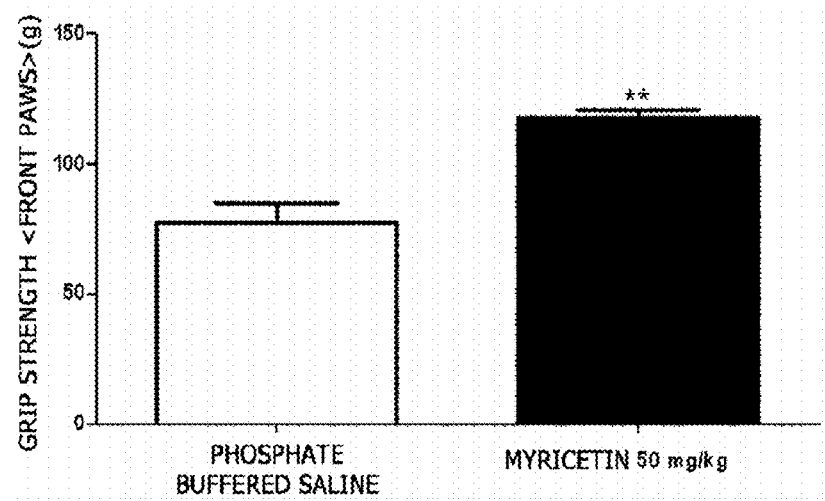
FIGS. 2A and 2B are graphs showing the strengthening of grip strength of a mouse due to myricetin intake.
Figure 2B:
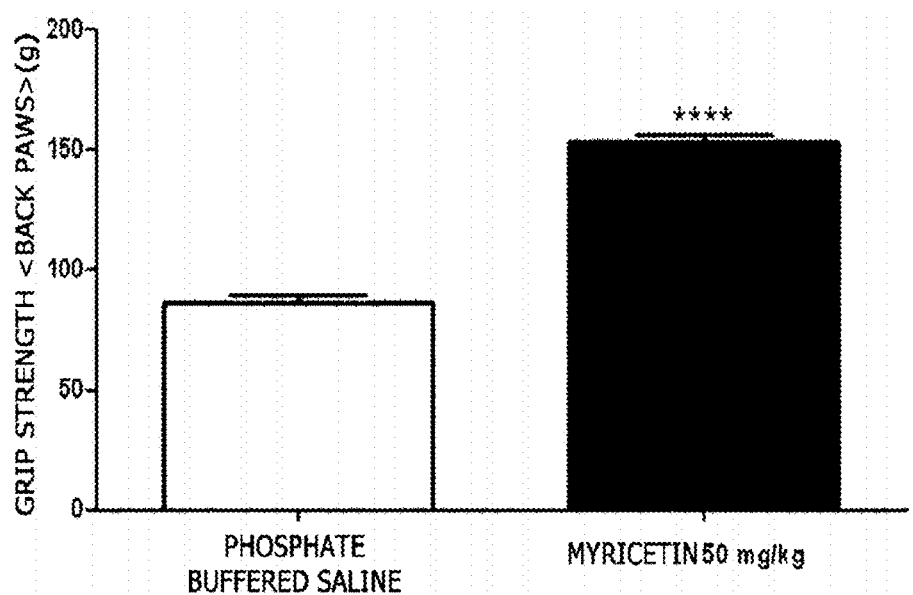

As a result, as shown in FIGS. 2A and 2B, it was noted that the maximum muscle strength of the myricetin-administered animal was increased. Accordingly, it was determined that the myricetin intake contributes greatly to enhance muscular strength.

Example 3

Measurement of Effect of Myricetin on Sensorimotor Function 3-1. Preparation of Myricetin-Administered Group and Negative Control To confirm an effect of myricetin on a sensorimotor function of a mouse, 8-week-old ICR mice were purchased from KOATECH, precultured for 1 week, and divided into two groups, each group having 5 mice. As described in Example 1, the experimental animals were divided into two groups, and then the first group was determined as a negative control, and to the second group, myricetin was orally administered daily at a concentration of 50 mg/kg using a 1 ml syringe for 2 weeks.

3-2. Measurement of Effect of Myricetin on Sensorimotor Function of Mouse

To measure an effect of myricetin on the sensorimotor function, a rotarod test (Panlab&Harvard, Spain) was performed on the mice in the control group and the myricetin-administered group. The rotarod test was performed to measure motor coordination (exercise adaptation) and a sense of balance of the animal (Michel Pratte et al., Behavioural brain research 216:313-320, 2011; Medina R. et al., FEBS Lett. 180(1): 77-80, 1985).

A tail of the mouse was put on a rotarod, and a speed of the rotarod was increased from 4 to 40 rpm within 5 minutes by an increase of 4 rpm at 30-second intervals. The time during which the mouse stayed on the rotarod was measured. The experiment was repeated five times, and the time during which the mouse stayed the longest on the rotarod was used as a result value. A significance of the experiment result was verified by performing a t-test on each of the test group and the control group, and the result showed a statistically significant difference (**$p<0.005$).

Figure 3:
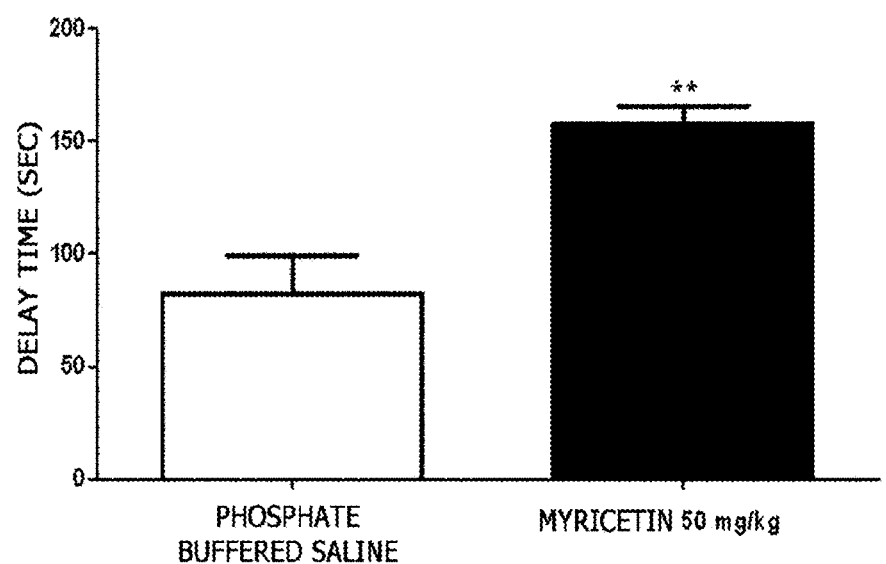
FIG. 3 is a graph showing the enhancement in sensorimotor function of a mouse duet to myricetin intake.
Figure 4A:
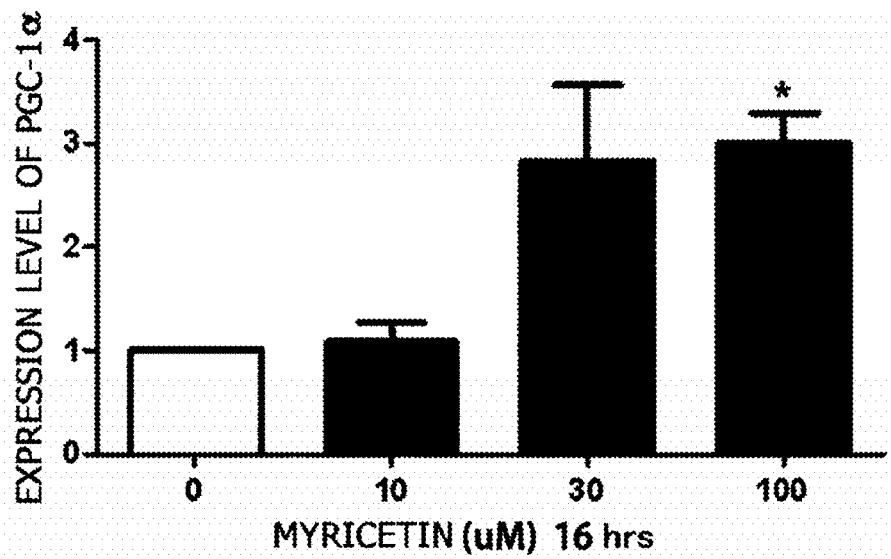
FIGS. 4A-4D relate to effects of myricetin on a mouse myotube.
Figure 4B:
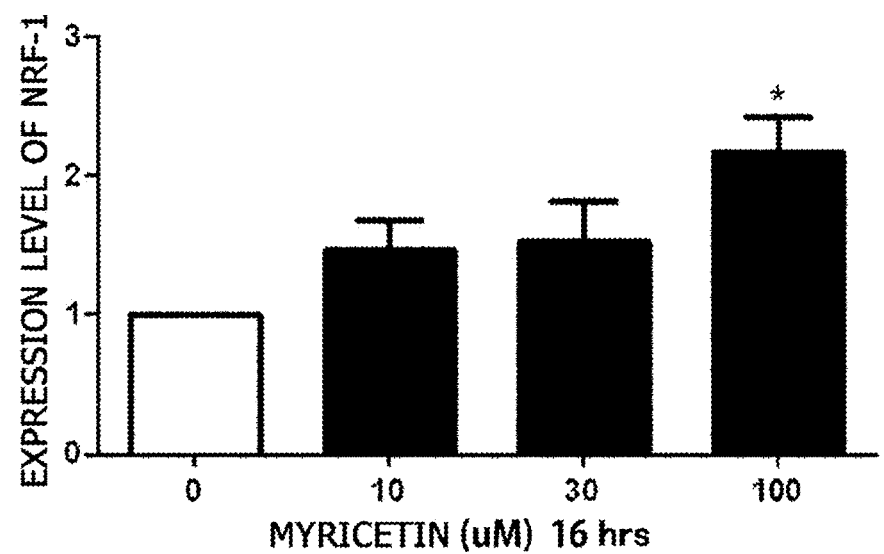
Figure 4C:
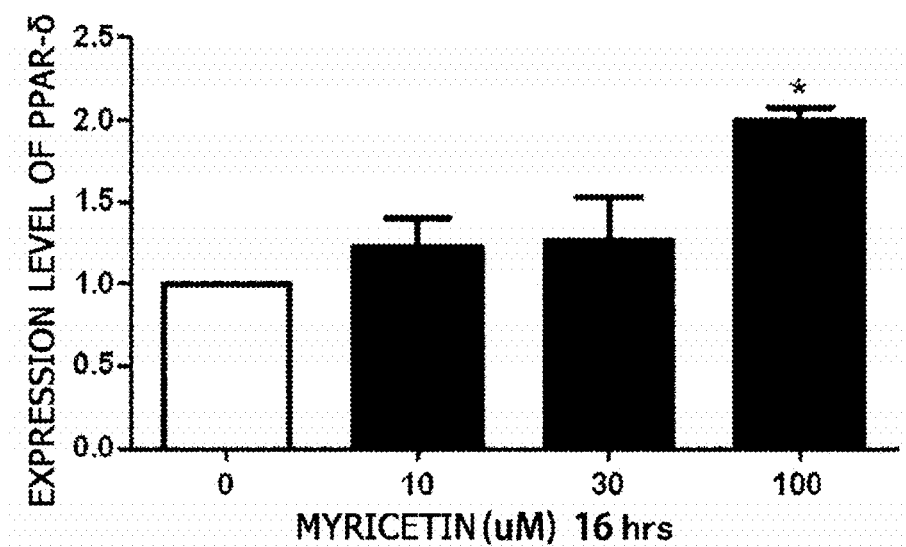
Figure 4D:
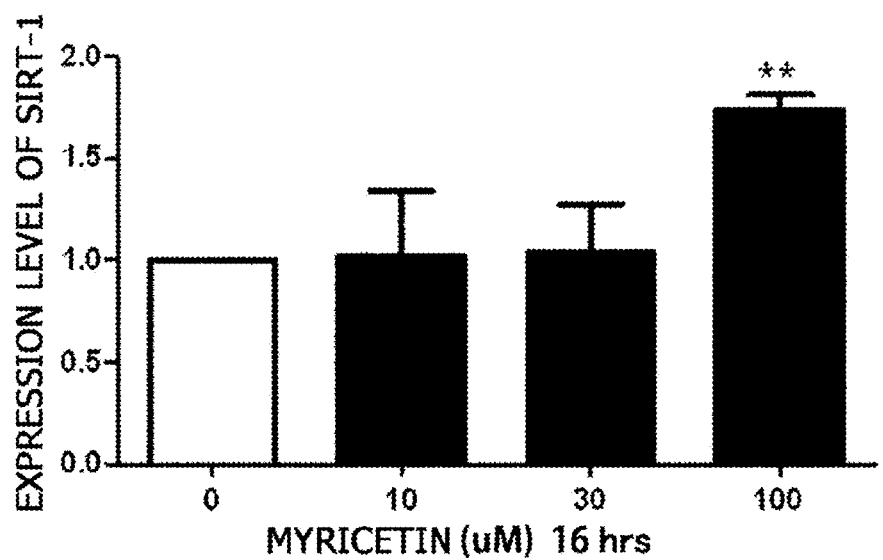

As a result, as shown in FIG. 3, it was noted that the myricetin-administered animals can stay longer on the rotarod. Therefore, it was noted that myricetin has an effect on enhancing motor coordination and a sense of balance.

Example 4

Measurement of Expression of Genes Involved in Biosynthesis and Function of Mitochondria in Cells According to Myricetin Treatment 4-1. Functions of Genes Peroxisome proliferator-activated receptor γ coactivator-1α (PGC-1α) and nuclear respiratory factor-1 (NRF-1) genes are representative genes involved in the transcription regulating the biosynthesis and function of mitochondria, and known to regulate the function and oxidative metabolism of mitochondria when activated (Christoph Handschin et al., Endocrine Reviews, 27:728-735, 2006). Accordingly, when expression levels of the PGC-1α and NRF-1 genes were measured, the enhancement in the biosynthesis and function of the mitochondria can be measured. Therefore, in the experimental example, when myricetin was used as a treatment, the expression levels of the PGC-1α and NRF-1 genes in the mouse myotube were observed.

A peroxisome proliferator-activated receptor-δ (PPAR-δ) gene is well known as a target for enhancing exercise capacity even when a mouse did not exercise (Vihang A. Narkar et al., Cell, 134:405-415, 2008). Accordingly, when an expression level of the PPAR-δ gene was measured, the possibility to be used as an ergogenic aid may be estimated. Therefore, in this example, when myricetin was treated, the expression level of the PPAR-δ gene in the mouse myotube was observed.

A silent mating type information regulation-2 homolog 1 (Sirtuin-1; SIRT-1) gene is a representative gene involved in the prevention of aging, and known to be used as a main regulatory factor for energy and metabolic homeostasis (Johan Auwerx et al., Cell, 127:1109-1122, 2006). Accordingly, when an expression level of the SIRT-1 gene was measured, a cell aging rate may be measured. Therefore, in this example, when myricetin was treated, the expression level of the SIRT-1 gene was observed.

In addition, when the function of the mitochondria is enhanced, energy production is increased, and fatigue recovery is achieved. Therefore, when the expression levels of the PGC-1α, NRF-1, PPAR-δ, and SIRT-1 are measured, a fatigue recovering effect may be estimated.

The improvement in the function of the mitochondria means that the energy consumption and energy efficiency are increased, and thus the antiobesity effect may be achieved. Accordingly, when the expression levels of the PGC-1α, NRF-1, PPAR-δ, SIRT-1 are measured, the antiobesity effect may be estimated.

4-2. Polymerase Chain Reaction (PCR)

Mouse myoblasts were purchased from the Korean Cell Line Bank (KCLB), and base sequences of primers for β-actin, SIRT-1, PGC-1α, NRF-1 and PPAR-δ genes were as follows:

◆β-actin (SEQ. ID. NO: 1)
forward: GGG AAG GTG ACA GCA TTG (SEQ. ID. NO: 2)
reverse: ATG AAG TAT TAA GGC GGA AGA TT

◆SIRT-1

(SEQ. ID. NO: 3)
forward: GTT AGC CTT GTA TTA TGG AGA TGA (SEQ. ID. NO: 4)
reverse: TGA GGT AAC TGT TTG AAA

◆PGC-1α

(SEQ. ID. NO: 5)
forward: AAG GAC TCT GAG AAC ACT TG (SEQ. ID. NO: 6)
reverse: CAA CTG ACC CAA ACA CTT TAC

◆NRF-1

(SEQ. ID. NO: 7)
forward: CCT CAG CCT CCA TCT TCT (SEQ. ID. NO: 8)
reverse: GAC CTT ACA ACC AAG CAA CT

◆PPAR-δ

(SEQ. ID. NO: 9)
forward: CCT CTC TCC CAC TCA CTT (SEQ. ID. NO: 10)
reverse: CCA CTT GAA GCA GCA GAT $1 \times 10^7$ $C_2C_{12}$ (mouse myoblasts) differentiated into myotubes using 2% horse serum made from the root canal. The mouse myotube was treated with myricetin by concentration and cultured for 16 hours, RNA was extracted from the myotube using TRizol, and then cDNA was synthesized through reverse transcription PCR (RT-PCR).

Real time PCR was performed using β-actin as a control and the primers for respective genes (95° C. for 3 minutes, <95° C. for 10 seconds, 60° C. for 10 seconds, 72° C. for 30 seconds>–39 cycles, 95° C. for 10 seconds, 65° C. for 5 seconds). The PGC-1α, NRF-1, PPAR-δ, and SIRT-1 were corrected with the β-actin, and the resulting value was obtained. The experiment result was comparatively assayed on the test group and the control group through one way ANOVA, the significance was verified by performing the Turkey's multiples comparison test (Turkey method) as post-testing, and the result showed a statistically significant difference (*$p<0.05$, **$p<0.005$).

As a result, as shown in FIGS. 4A, 4B, 4C and 4D, in the test groups treated with 10, 30 and 100 μM myricetin, compared to the control group, the expression of SIRT-1, PGC-1α, NRF-1 and PPAR-δ were increased two to three times.

From the result, it was noted that the treatment with myricetin of the present invention increases the expression of the PGC-1α and NRF1 genes regulating the biosynthesis and function of mitochondria, and activates a target for enhancing exercise capacity, PPAR-δ, and an antiaging-related gene, the SIRT-1 gene. Accordingly, it was determined that the myricetin enhances the function of the energy producing organ in cells, the mitochondria, to achieve a physical strength enhancing effect.

Example 5

Measurement of Effect of Myricetin on Antiaging

While the inventors performed an experiment to confirm effects of myricetin on enhancing an exercise function and a sensory function, they found that the mice to which myricetin was administered lost weight, and to confirm the weight loss, an additional experiment was performed on the rats as follows.

7-week-old SD rats were purchased from KOATECH, precultured for 1 week, and randomly divided into two groups, each group having 5 rats. First, 50 mg/kg of myricetin was administered into the test group, and phosphate buffered saline was administered into the control group for 5 days.

5-1. Measurement of Change in Body Weight of Myricetin-Taked Mouse

Figure 5A:
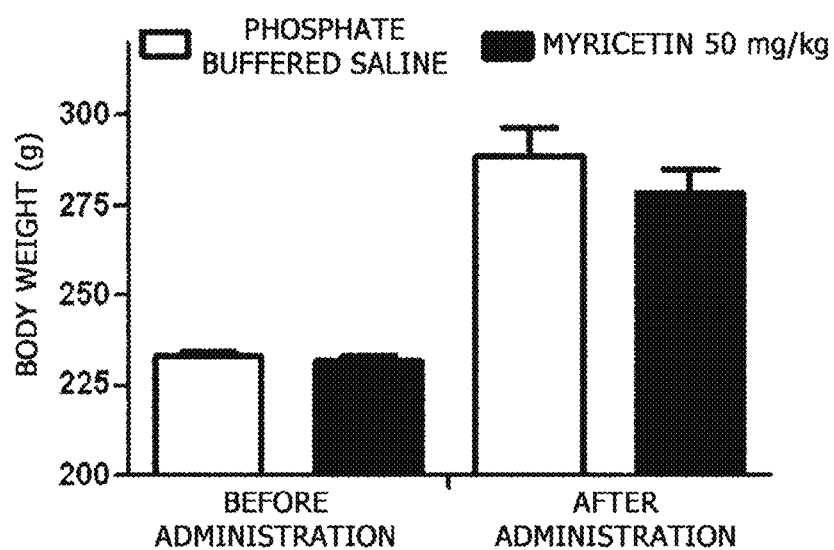
FIGS. 5A and 5B relate to effects of myricetin on a body weight and appetite of an SD rat when myricetin is administered.

A change in body weight was measured using an electric measure (CAS, China). Before administration, the body weights of the rats in each group were the same as 225 g on average, but after the end of the experiment, the body weights of the rats in the control group were 285 g on average, and the body weights of the rats in the myricetin-administered group were 275 g on average (FIG. 5A). As a result, as shown in FIG. 5A, it was observed that the body weight of the myricetin-administered mouse was lower than that of the mouse to which the phosphate buffered saline was administered.

5-2. Measurement of Food Intake of Myricetin-Taken Mouse

Figure 5B:
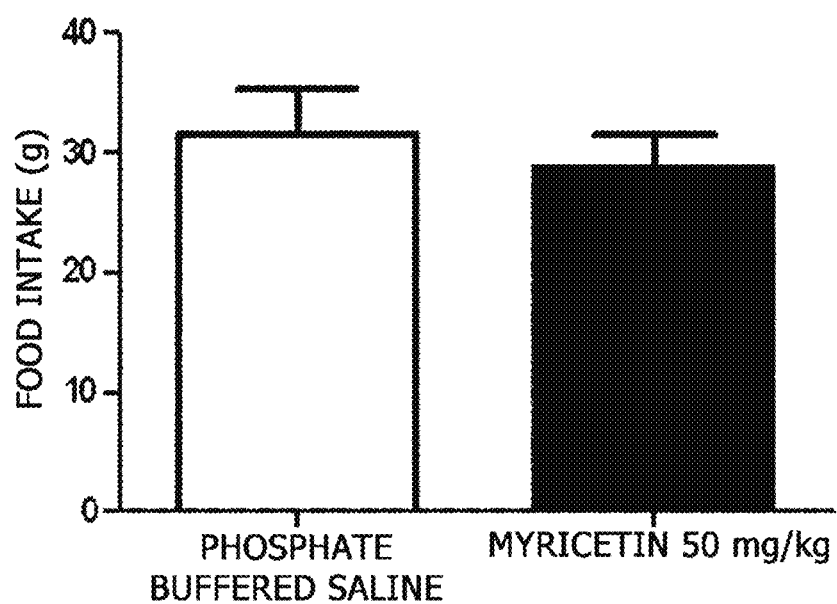

The investigation of food intake was performed by automatically measuring the daily food intake of the phosphate buffered saline-administered mouse and the myricetin-administered mouse using an action metabolism meter (Panlab&Harvard, Spain). The average food intake was determined as an average food intake of each of the five rats in one group. As a result, as shown in FIG. 5B, it was observed that the myricetin-administered mouse was smaller than that of the phosphate buffered saline-administered mouse.

The result showed that the myricetin administration reduces a body weight of the mouse by appetite suppression, and thus it shows that myricetin can be used as an antiobesity medicine.

The above description of the present invention is exemplary, and it would be understood that the present invention can be modified in a different particular type without changing the technical idea or essential characteristics of the present invention by those of ordinary skill in the art. Therefore, it should be understood that the above-described examples are exemplary in every aspect, but not limited.

According to the present invention, a composition containing myricetin or a pharmaceutically available salt thereof as an active ingredient enhances exercise capacity and physical strength, prevents aging, enhances recovery from fatigue, improves the function of mitochondria to increase energy efficiency and energy consumption, and therefore also has an antiobesity effect. For this reason, the composition is expected to be significantly applied to a functional food or medicine field.

What is claimed is:

1. A method of treatment for enhancing exercise capacity, the method comprising:
   orally administering, to a subject in need of such treatment, an effective amount of myricetin or a pharmaceutically acceptable salt thereof; and
   subsequently estimating expression by PCR of a peroxisome proliferator-activated receptor γ coactivator-1α (PGC-1 α), nuclear respiratory factor-1 (NRF-1), or peroxisome proliferator-activated receptor-δ (PPAR-δ) gene or sirtuin-1 (SIRT-1) gene.

2. The method of claim 1, wherein the oral administration is repeated for an extended period.

3. The method of claim 2, wherein the extended period is at least 2 weeks.

4. The method of claim 2, wherein the effective amount per day is from 0.01 to 100 mg for 1 kg of the subject's weight.

5. The method of claim 2, wherein the effective amount per day is 50 mg for 1 kg of the subject's weight.

* * * * *

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
gggaaggtga cagcattg                                                       18

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
atgaagtatt aaggcggaag att                                                 23

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
gttagccttg tattatggag atga                                                24

<210> SEQ ID NO 4
<211> LENGTH: 18
<212> TYPE: DNA
<213> ORGANISM: Artificial Sequence
<220> FEATURE:
<223> OTHER INFORMATION: primer

<400> SEQUENCE: 4
tgaggtaact gtttgaaa                                                       18
```

```
<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
aaggactctg agaacacttg                                                    20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
caactgaccc aaacacttta c                                                  21

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
cctcagcctc catcttct                                                      18

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gaccttacaa ccaagcaact                                                    20

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
cctctctccc actcactt                                                      18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
ccacttgaag cagcagat                                                      18
```